US009029736B2

(12) United States Patent
Lavin, Jr.

(10) Patent No.: US 9,029,736 B2
(45) Date of Patent: May 12, 2015

(54) ELECTRONIC PERSONAL THERMAL CONTROL APPARATUS AND SYSTEM

(75) Inventor: Edward F. Lavin, Jr., Houston, TX (US)

(73) Assignee: My Core Control Development, LLC, Houston, TX (US)

( * ) Notice: Subject to any disclaimer, the term of this patent is extended or adjusted under 35 U.S.C. 154(b) by 0 days.

(21) Appl. No.: 13/525,969

(22) Filed: Jun. 18, 2012

(65) Prior Publication Data

US 2012/0318781 A1 Dec. 20, 2012

Related U.S. Application Data

(60) Provisional application No. 61/498,319, filed on Jun. 17, 2011.

(51) Int. Cl.
| H05B 1/00 | (2006.01) |
| H05B 3/00 | (2006.01) |
| H05B 11/00 | (2006.01) |
| H05B 3/06 | (2006.01) |
| A41D 13/005 | (2006.01) |

(52) U.S. Cl.
CPC .................................. *A41D 13/005* (2013.01)

(58) Field of Classification Search
CPC ........... A41D 13/005; H05B 2203/017; H05B 2203/036; H05B 3/342
USPC ......... 219/211, 212, 527, 529–530, 544–549; 607/99, 108–112; 62/259.3
See application file for complete search history.

(56) References Cited

U.S. PATENT DOCUMENTS

| 5,032,705 A | 7/1991 | Batcheller et al. |
| 5,653,741 A * | 8/1997 | Grant ............................ 607/114 |
| 5,800,490 A * | 9/1998 | Patz et al. ..................... 607/108 |
| 5,840,080 A | 11/1998 | Der Ovanesian |
| 6,005,222 A * | 12/1999 | Hicks ............................. 219/211 |
| D464,140 S | 10/2002 | Lavin, Jr. |
| 6,514,279 B1 | 2/2003 | Lavin, Jr. |
| 6,727,469 B1 * | 4/2004 | Parker et al. .................. 219/211 |
| 6,927,316 B1 | 8/2005 | Faries, Jr. et al. |
| 7,186,957 B2 * | 3/2007 | Martin .......................... 219/529 |
| 2001/0045104 A1 | 11/2001 | Bailey, Sr. et al. |
| 2009/0289046 A1 * | 11/2009 | Richmond .................... 219/211 |
| 2010/0198322 A1 | 8/2010 | Joesph et al. |

OTHER PUBLICATIONS

International Search Report and Written Opinion for PCT/US2012/042950 dated Aug. 30, 2012.

* cited by examiner

*Primary Examiner* — Dana Ross
*Assistant Examiner* — Lindsey C Teaters
(74) *Attorney, Agent, or Firm* — Winstead PC

(57) ABSTRACT

An electronic personal thermal control apparatus and method may provide heating and cooling for a user. A power source may provide power to a thermal module that is capable of heating or cooling a heat transfer component to a desired temperature. The heating or cooling may be managed by a controller. The components may be placed in a housing. The apparatus may be placed at any suitable position on a user's body, such as the wrist or ankle(s). The housing of the apparatus may be incorporated or combined with clothing, such as wristband(s), apparel, jackets, footwear, or the like.

20 Claims, 11 Drawing Sheets

ELECTRONIC PERSONAL THERMAL CONTROL APPARATUS AND SYSTEM

RELATED APPLICATIONS

This application claims the benefit of U.S. Provisional Patent Application No. 61/498,319 to Edward F. Lavin, Jr., filed on Jun. 17, 2011, which is incorporated herein by reference.

FIELD OF THE INVENTION

This invention relates to a personal thermal control apparatus. More particularly, a effective and long term use personal thermal control apparatus.

BACKGROUND OF INVENTION

In cold or hot climates, it may be desirable to provide heating or cooling for personal comfort to an individual. For example, personal heating or cooling may be desired during activities such as skiing, camping, hiking, fishing, hunting, working, athletic activities, military and the like. In some instances, application of heating or cooling to injuries, sore muscles or in joints in cooling the blood to minimize brain damage, and the like may provide a therapeutic effect.

There are several known prior art apparatuses for providing personal heating and/or cooling for an individual. For example, U.S. Pat. No. 5,766,235, U.S. Pat. No. 5,514,170, and U.S. Pat. No. 6,514,279 provide various personal apparatuses. Prior art heated outerwear may utilize less efficient resistive heat and delivers the heat to areas of the body like the midsection or chest area. While heating the midsection or chest area provides heating, it does not effect a core body temperature change. Core body temperature changes are measurable orally by thermometer.

Personal thermal control devices, such as described herein, provide body temperature change. The thermal fluids or gels that may be utilized in other devices allows for a limited duration that the device may be utilized until the thermal energy is exhausted. Further, immediately upon use, the temperature of the device steadily increases or decreases as the thermal gel is heated or cooled by the user's body. Recharging the device for cooling may require placement in a freezer for a significant amount of time or replacement with a substitute thermal storage packet that has previously cooled. Other known devices that utilize electronic heating have short running times and do not efficiently heat the body.

The personal thermal control apparatuses and methods discussed herein provide heating and/or cooling utilizing thermal module. These apparatuses are positioned at the inner wrist pulse point area and or the inner ankle pulse point area in close proximity to major vasculature located at the skins surface and externally delivers constant thermal energy, hot or cold to a thermal plate designed to maximize surface area contact with the blood vessels near the apparatus that transporting blood in both directions at core body temperature. Heat transfer occurs with the blood, and the circulatory system distributes blood throughout the body. The circulation of heated/cooled blood provides the desired counter active change in core body temperature desired by the wearer. These personal thermal control apparatuses provide for efficient electric operation to reduce size and power requirements. The apparatuses provide improved operation time. In some embodiments, photo voltaic patches may be used in conjunction with a battery and could provide perpetual operation.

SUMMARY OF THE INVENTION

An illustrative implementation of an electronic personal thermal control apparatus and method may provide heating and cooling for a user. A power source may provide power to a heating/cooling module that is capable of heating or cooling a heat transfer component to a desired temperature. The heating or cooling may be managed by a controller. The components may be placed in a housing. In some embodiments, the apparatus and method may utilize a photo voltaic cell to power the apparatus, charge the power source, or both. The apparatus may be placed at any suitable position on a user's body, such as the wrist or ankle(s). The housing of the apparatus may be incorporated or combine with clothing, such as wristband(s), shirts, footwear, or the like.

In another illustrative implementation, a personal thermal control apparatus provides a power source, and at least one heating/cooling module powered by the power source. The heating/cooling module may provide a thermoelectric element. When a first voltage polarity applied to the thermoelectric element, it causes a first side of the thermoelectric module to increase in temperature, and when a second voltage polarity applied to the thermoelectric element, it causes said first side of the thermoelectric element to decrease in temperature. The apparatus may also provide a heat transfer element coupled to said first side of the thermoelectric module, and a controller coupled to the power source and the thermoelectric module, wherein the controller manages the voltage applied to the thermoelectric module.

In yet another illustrative implementation, a personal thermal control apparatus provide a rechargeable battery; a first heating/cooling module for heating or cooling, and a controller coupled to the rechargeable battery and the first heating/cooling module, wherein the controller manages the voltage applied to the heating/cooling module. The first heating/cooling module includes a first housing; a first heating/cooling module is positioned in the first housing, wherein the first heating/cooling module is powered by the rechargeable battery; and a first heat transfer element coupled to a first side of the thermoelectric module.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
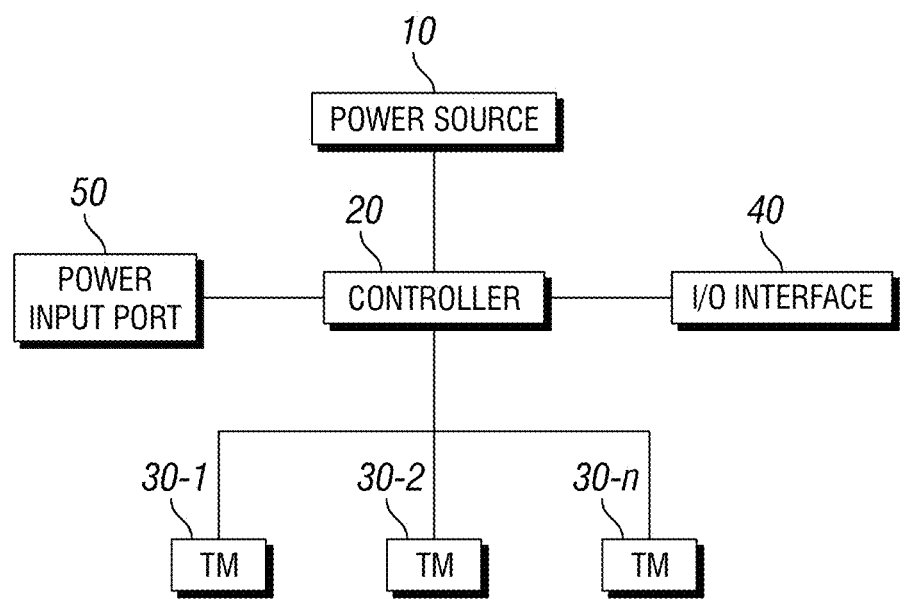
FIG. 1 is an illustrative diagram of the electronic components of a personal thermal control apparatus.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

The personal thermal control apparatuses and methods discussed herein provide for effecting core body temperature changes in humans for long durations. The apparatus may electronically provide heating or cooling to a focused specific area of the human body. As a nonlimiting example, heating/cooling module may be strategically positioned directly over major blood vessels and capillary beds located at the pulse points of the wrist, ankle, or other areas of the human body. The average core body temperature for humans can be raised or lowered effectively through thermodynamic heat absorption by the blood that flows through the major blood vessels and capillaries located just under the skins surface with-in a specific surface area located at the pulse points of the wrist and ankle areas.

In one embodiment the heating/cooling module may be a thermoelectric element. Thermoelectric elements allow an electrical potential to create a temperature difference or a temperature difference to create an electrical potential. The apparatus may utilize thermoelectric element(s) for heating/cooling by applying a voltage to the element. The polarity of the applied voltage provided to the thermoelectric element determines whether heating or cooling is provided. In some embodiments, the heating/cooling module may also provide a resistive heating element.

Personal thermal control apparatuses provide the ability to effectively raise or lower human core body temperature on demand. Men, women and children of all ages may use personal thermal control apparatus in their daily lives to provide heating or cooling as desired for long durations of time. Personal thermal control apparatuses may be incorporated into apparel, outerwear, coats, jackets, sweaters, windbreakers, shirts, pants, shorts, wristbands, footwear, combinations thereof, and the like. The personal thermal control apparatus is suitable for a wide range of activities, such as sports, recreation, work, camping, fishing, hiking, and military use. The personal thermal control apparatus may also be utilized in medical applications requiring hot or cold treatments. For example, the apparatus may be utilized to fight inflammation, high fever, stabilization and minimization of brain damage after strokes, head injury, or the like.

The personal thermal control apparatus may utilize heating/cooling modules to allow for significantly increased operating duration. Further, the personal thermal control apparatus is capable of maintaining consistent temperature throughout use. Various features of the device provide improved functionality that allows the device to efficiently reduce or increase a user's core body temperature. By using a thermal module to heat or cool a thermal plate or similar size, effective heating or cooling for the wearer can be realized using a very low current. The low power requirements of the apparatus allow it to operate for longer durations (e.g. 24 hours or more) than prior art apparatuses. By incorporating photo voltaic/solar power, the duration of operation can be extended even further and may potentially allow for perpetual operation. Perpetual or extended operation is particularly useful when access to a plug-in power source is not available. For example, perpetual or extended operation may be highly beneficial in military applications.

FIG. 1 is an illustrative diagram of the electronic components of a personal thermal control apparatus. The apparatus may provide a power source 10, controller 20, thermal module(s) 30-1, 30-2, 30-n, I/O interface(s) 40, and power input port 50. Power source 10 provides electric power for the apparatus. Power source 10 may be an external source, solar panels, batteries, rechargeable batteries, and/or the like. Non-limiting examples of suitable batteries may include NiCd, NiMH, and Li-ion batteries. In one embodiment, the battery 10 may be a 3.7V. The battery may also be a 2,500 mAh Li-ion battery. Power source 10 is coupled to controller 20, which routes power to thermal module(s) 30 or I/O interface(s) 40 and manages charging of the battery. Controller 20 manages various operations of the apparatus such as, but not limited to, heating/cooling management, charging, operation modes, communication with I/O interface(s), and the like. In some embodiments, heating/cooling management may be governed by sensors that constantly monitors core body temperature of the wearer, and the controller 20 adjusts to heating or cooling as needed to counteract adverse climate conditions. Controller 20 may be a microprocessor, processor, CPU, integrated circuit, or a combination thereof that may be programmed for operation of the apparatus as discussed herein. For example, controller 20 may provide functionality such as battery monitoring (including voltage and current monitoring), battery status indication (e.g. low battery or charging), function status indication (e.g. charging, cooling, or heating), built in charging circuitry, and the like.

Thermal module(s) 30 may provide heating and/or cooling in accordance with a voltage applied to the element by controller 20. Controller 20 may apply voltage to one or more of the thermal module(s) 30 as desired. Thermal module(s) 30 may be strategically positioned to maximize efficiency of the heat transfer to a user. For example, the thermal module(s) 30 may be a Laird Technologies model number Cp 08, 63, 06L thermoelectric chip. In contrast to other personal thermal control devices, the thermal module(s) 30 operate using relatively small power source (e.g. 3.7V battery). In some embodiments, the thermal module(s) 30 may also provide a resistive heating element. I/O interface(s) 40 allow the apparatus to be connected to interfaces that allow a user to operate, control, and/or manage the apparatus. I/O interface(s) 40 may provide ports for external devices (e.g. cell phones, portable music devices, other portable electronics, or the like). I/O interface(s) 40 may also provide control buttons/interfaces. For example, control buttons may allow a user to select modes of operation (e.g. heating or cooling); settings for the heating or cooling modes—low (50% power), mid (75% power), high (100% power); or the like. As another example, the apparatus may include control interfaces, a display, visual indicators, audio indicators, combinations thereof, and the like. In a non limiting embodiment, I/O interfaces 40 may include a on/off button and visual indicators to indicate charging status, heating or cooling, operation mode (e.g. low, mid, high), power source the devices is utilizing, or the like. Charge port 50 may provide a connector that allows the apparatus to be connected to an external power source suitable for charging. For example, the charge port 50 may be suitable for connection to an AC power source, 2.0 amp connector, USB connector, or any suitable electric connector. In some embodiments, charge port 50 may also provide coupling to portable power source, such as solar cells or an external battery.

In some embodiments, the apparatus may provide additional features such as a pedometer, clock, stopwatch, display, time/distance/steps information, GPS location, blue tooth or other communication technology and/or other features.

Figure 2A:
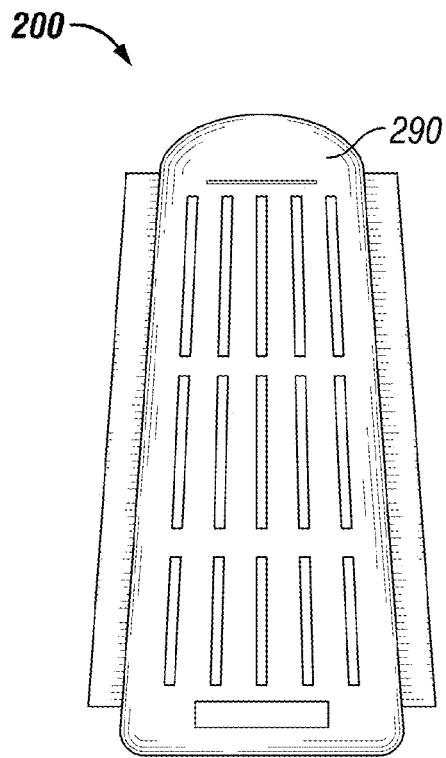
FIGS. 2A-2C are an illustrative implementation of an embodiment of a heating/cooling module.
Figure 2B:
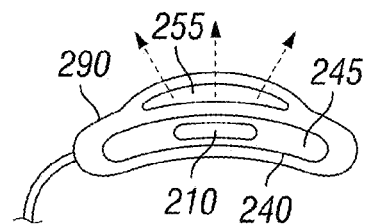
Figure 2C:
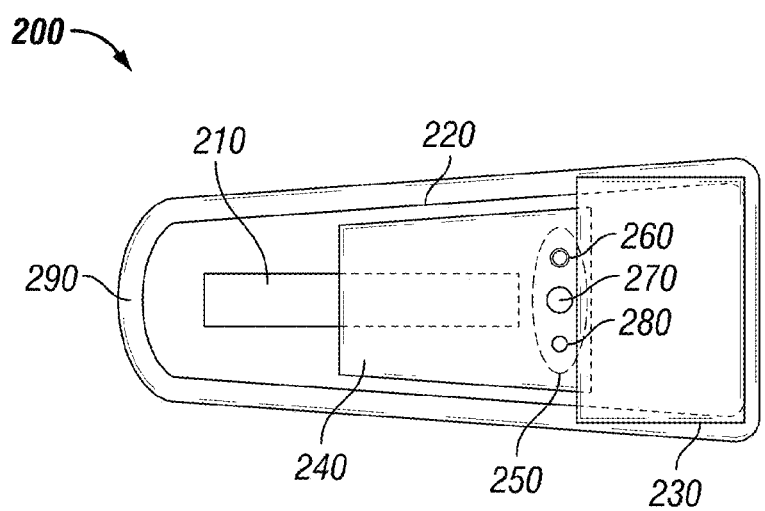
Figure 3A:
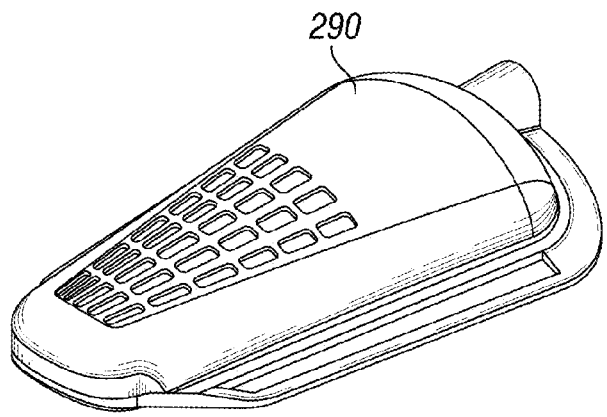
FIGS. 3A-3D are an illustrative implementation of another embodiment of a heating/cooling module.
Figure 3B:
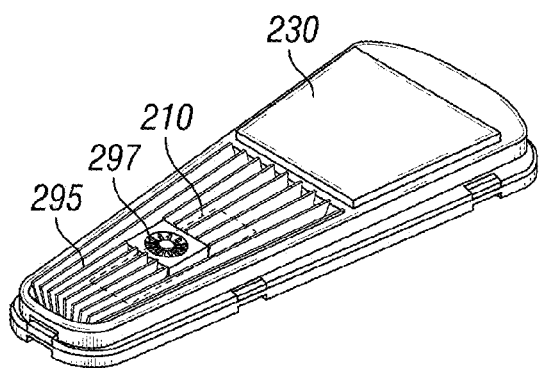
Figure 3C:
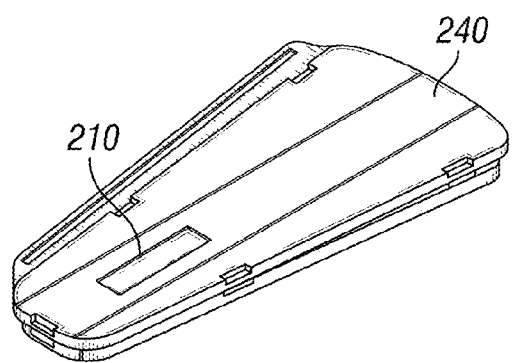
Figure 3D:
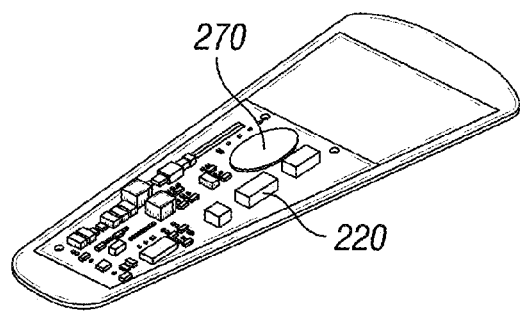

FIGS. 2A-2C are illustrative diagrams of an embodiment of a heating/cooling module 200 with a controller, power source, and user interface. In some embodiments, thermoelectric module 200 may be referred to as a main heating/cooling module. The heating/cooling module 200 may provide a thermal module 210, controller board 220, battery 230, thermal plate 240, and user interface 250. Heating/cooling module 200 may be strategically positioned directly over major blood vessels and capillary beds, located at the pulse points of the human body, such as the wrist and ankle area, to efficiently provide personal thermal control for a user. For example, the thermoelectric module 200 may be utilized for a wristband that cools the blood vessels in the wrist of the user.

Thermal module 210 may utilize electrical energy to heat or cool the bottom portion of the wristband. For example, thermal module 210 may be a thermoelectric chip that provides heating when a voltage is applied and cooling when a reverse polarity is applied. Thermal module 210 may be metalized on the surface for improved attachment to optional heat sink(s). Further, in some embodiments, thermal module 210 may also provide a resistive heating element. Thermal module 210 may be electronically coupled to a controller board 220. Controller board 220 is a circuit board that manages operation of a thermoelectric apparatus, which may include controllers, processors, memory, modules, various electronic components, or combinations thereof. Controller board 220 may also be coupled to a power source, such as a battery 230 or an external power source. Battery 230 provides a portable power source that powers the apparatus. Battery 230 may provide sufficient power to operate up to 24 hrs. When battery power is low, an external power source may be utilized to recharge battery 230 and/or power the apparatus.

The controller board 220 is coupled to the thermal module 210 and battery 230. Based on the settings selected, the controller board 220 controls the power provided to the thermal module 210. For example, when a desired temperature is selected, the controller may manage the amount of power provided to the thermal module 210 to achieve the desired temperature. Additionally, the controller board 220 can manage additional features, such as battery charging, light indicators, or the like.

A controller (e.g. CPU, microprocessor, or the like) provided by controller board 220 may controls the functions provided by the apparatus. These functions include, but are not limited, to battery connections, charging, power on off control, photo voltaic management, indicator operation, power provided to each thermal module, and other desired functions.

Plate 240 may preferably be in contact with thermal module 210 to maximize thermal transfer. Plate 240 may be formed from a material with high thermal efficiency or high thermal conductivity. For example, plate 240 may be copper or aluminum. Plate 240 is positioned in housing 290 to minimize the distance between the plate and the user. For example, in the embodiment shown, plate 240 is positioned below controller board 220 and thermal module 210 in a region that is closest to area that contacts the user. The plate 240 may provide a surface area specifically shaped to maximize the heat absorption for heating or cooling blood vessels. For example, plate 240 may be long and thin to maximize the contact area between the plate and the blood vessels in a user's wrist or ankles. In some embodiments, a thermal gel (not shown) that is in contact with the plate may be provided to aid thermal energy transfer. For example, a band surrounding the ankle or wrist may contain a thermal gel to further assist heat transfer to a user. Further, in other embodiments, a thermal gel may be substituted in place of a plate. Similar to the heat transfer plate, the thermal gel may be positioned at a desirable position of a person's body, such as on the wrist, ankles, or any other suitable position.

In a region above plate 240, insulator material 245 is provided to minimize undesired heat transfer from the plate to other parts of the module. Insulator material 245 allows the majority of the heating or cooling to be absorbed by the user. Due to the temperature difference that is generated by thermal module 210, a side opposite plate 240 may provide a different temperature. For example, when cooling is desired the side of thermal module 210 coupled to heat transfer plate 240 is cool, and the opposite side is hot. In order to dissipate the undesirable heat, a vent 255 in housing 290 is provide to allow heat to dissipate out from the module. In some embodiments, a heat sink (not shown) may optionally be provided on top of thermal module 210 to aid heat dissipation. For example, when thermal module 210 utilizes components that generate heat when cooling, it may be desirable to provide a heat sink to aid heat dissipation.

The user interface 250 provides I/O interface(s) for the user to operate the apparatus. For example, in the embodiment shown, the user interface may include a charge port 260, button 270, and LED indicator 280. The charge port 260 provides power to the apparatus, charges the power source, or both. The charge port 260 may be connected to a suitable power source, such as a photo voltaic cell, AC power source, DC power source, or the like. Button 270 allows the user to control operation of the device. For example, button may be pressed to cycle through various modes of operation, such as low heating, medium heating, high heating, low cooling, medium cooling, high cooling, sensor mode to run off of the wearer's core body temperature and off mode. In some embodiments, it may be desirable to include additional inputs, buttons, switches, or the like. The I/O interfaces(s) may allow the apparatus to be turned on and off, select a mode, set the device to a desired temperature, and/or the like. The apparatus may include an LED indicator or display 280. In some embodiments, indicator(s) may be substituted with or include an LCD display, additional LEDs, light indicators, or the like. The LED indicator or display 280 may indicate when charging is occurring, when power is low, a temperature set by the user, an operating mode, whether the apparatus is operating on battery or external power, and/or the like.

Heating/cooling module 200 is surrounded by a housing 290 to protect the module. Housing 290 may be formed in any suitable shape desired. For example, housing 290 may be ergonomically shaped to comfortably fit around a user's wrists, ankles, or the like. Further, housing 290 may be shaped to maximize the contact area with the user's wrists, ankles, or the like. In some embodiment, housing 290 may be waterproof. For example, housing 290 may be a polycarbonate skeleton or the like. The housing 290 and plate 240 may be ergonomically designed for comfort and to provide efficient thermal transfer. A thin polycarbonate shell may be snapped into place over the electronic components, and then the entire thermoelectric module 200 is over molded. For example, the over mold may be a sanoprene rubber like material for durability, waterproofing, and to protect the device from other elements including human sweat. In some embodiments, housing 290 may provide an area for sewing or attach the thermoelectric module 200 to wristbands, apparel/outwear footwear, or other accessories.

By providing external electronically generated hot or cold from the apparatus to specific blood vessel(s) via a shaped surface area through a thermal conductive material plate positioned directly over pulse points, on demand externally generated hot or cold can be utilized to make a user more comfortable. By applying heat or cold to blood vessels, the user experiences more effective cooling or heating than apparatuses utilizing heat or cold applied to areas that are not close to major blood vessels. For example, heating/cooling module 200 may be positioned on arteries and/or veins near the wrist, ankles, other parts of the body with one or more blood vessels, or a combination thereof.

This new process may be utilized in several different consumer products that are focused on providing heating and/or cooling. The personal thermal control devices may be utilized in apparel (shirts, pants, shorts, etc.), outerwear (jackets, sweatshirts, sweaters, etc.), wrist bands, footwear, and other accessories.

The personal thermal control apparatus may be powered batteries, rechargeable batteries, solar power, external power sources, or a combination thereof. In one embodiment, the apparatus is battery powered. The apparatus may also provide an input port for receiving power from an AC or DC power source (e.g. to charge a rechargeable battery, to operate directly from the power source, or both) or photo voltaic/solar power cell(s). In one embodiment, the apparatus may utilize a 3.7V rechargeable lithium battery.

The apparatus may also provide one or more photo voltaic patches that may be utilized to generate power. For example, the patch may be sewn to sleeves or shoulders of apparel, provided on wrist bands, provided on footwear, or the like. The apparatus may be partially or fully powered by photo voltaic cell. The solar energy may power the device directly or may be utilized to charge and store power in the power source. The use of photo voltaic cells may provide extended operation time and may provide operation in areas where an external plug in power source is not readily available.

The photo voltaic cell patches may be positioned in locations that maximize solar exposure. The photo voltaic cells may be encapsulated in clear plastic and over molded in a rubber like material to create a lip that may be utilized to sew or attach the device to clothing or the like. A lens may be molded into the clear plastic cover to magnify the intensity of light onto the photo voltaic cell and may be used in conjunction with a holographic background to maximize reflectivity and in combination increase the light intensity and maximize the electrical current produced. Photo voltaic patches may be electronically coupled to the personal thermal control apparatus, such as by wiring or the like.

FIGS. 3A-3D are illustrative implementations of a heating/cooling module that incorporates a heat sink. Thermal module 210, controller board 220, battery 230, plate 240, and button 270 are provided as discussed in other embodiments. In some embodiments, it is desirable to provide a heat sink 295 placed on thermal module 210. It may also be desirable to provide a fan 297 to further aid heat dissipation. When thermal module 210 is utilized for cooling, a first side of thermal module is cooled and the opposite side becomes warm. Heat sink 295 increases heat dissipation from the warm side of thermal module 210. A top portion of housing 290 may be vented to allow through the housing to improve heat dissipation. The heat dissipation features of the thermoelectric module allow heat to be dissipated away from the module, thereby limiting or prevention absorption of heat by nearby components or the wearer's body.

Thermal insulation material and thermal reflectivity may be used throughout each aspect of the design to maximize performance. Clear polycarbonate material may be used in the frame or skeleton. The skeleton may utilize infrared reflective flecks molded in the polycarbonate to maximize thermal reflectivity inside and outside each device. Thermal insulation material may be used through out each device to maximize performance. Further, materials are selected to maximize product durability.

Figure 4A:
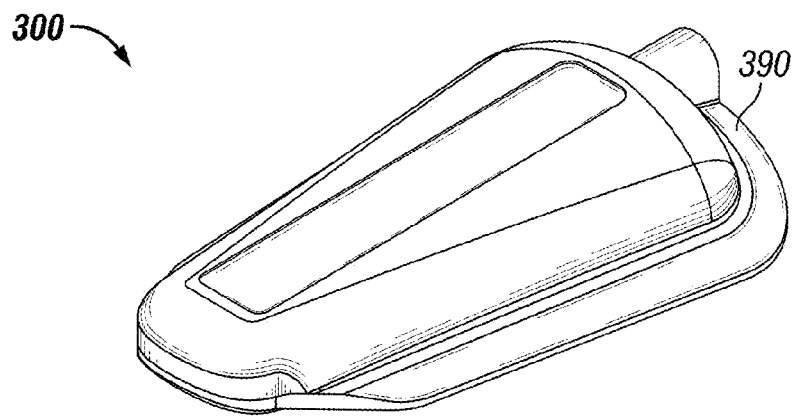
FIGS. 4A-4C are an illustrative implementation of an additional embodiment of a heating/cooling module.
Figure 4B:
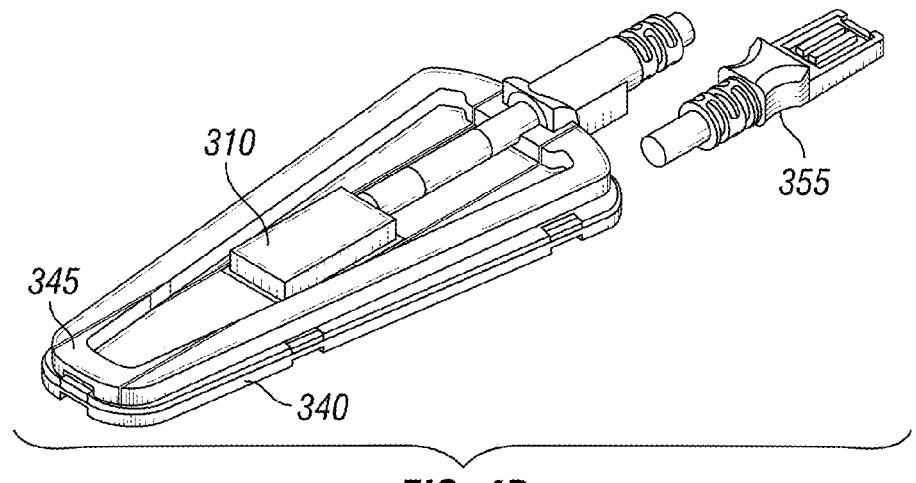
Figure 4C:
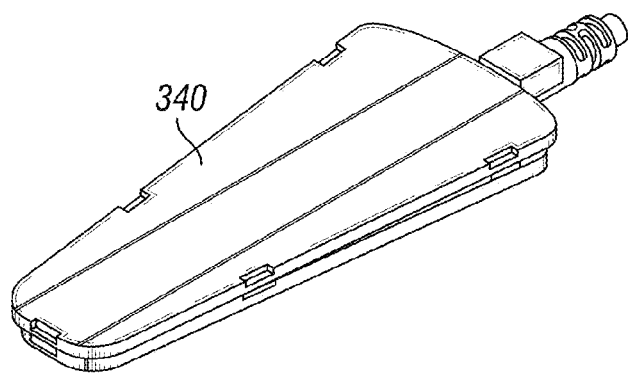

FIG. 4A-4C are illustrative implementations of additional heating/cooling modules 300 in a personal thermal control apparatus. Heating/cooling module 300 is a simplified module that does not provide a controller, battery, or user interface. As such, in some embodiments, the heating/cooling modules 300 may be referred to as a simplified thermoelectric module. In some implementations of a personal thermal control apparatus, it may be desirable to have more that one heating/cooling module. For example, it may be desirable to provide two or more thermoelectric modules in apparel such as a jacket, coat, outerwear, sweater, pants, or the like. When additional heating/cooling modules 300 are desired, the additional modules may be simplified to eliminate the controller board, battery, and interface provided in other embodiments. The additional heating/cooling modules 300 provide a thermal module 310, plate 340, insulation 345, and housing 390 providing the same functionality as discussed previously. Additional heating/cooling module 300 may provide connectors 355 that allow it to be connected to a controller that manages operation of each of the heating/cooling modules in the system.

Figure 5:
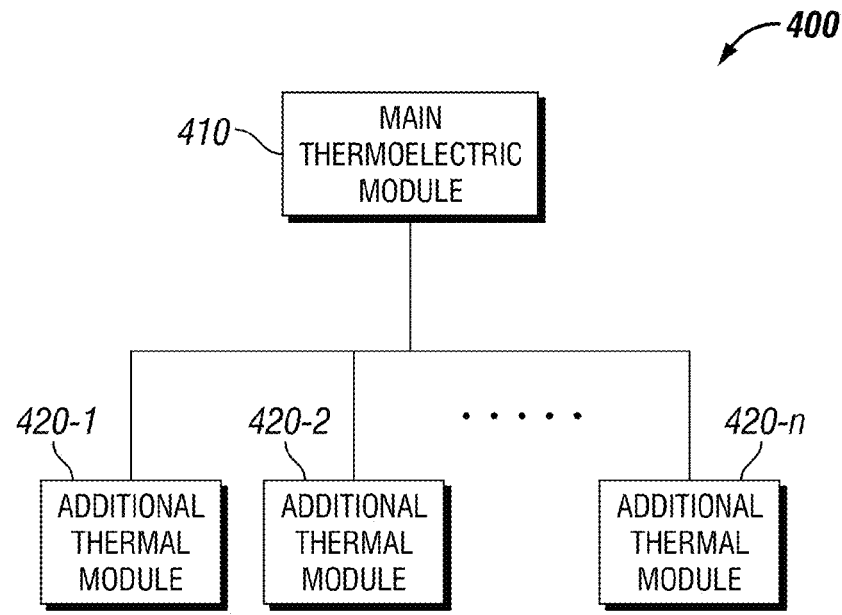
FIG. 5 is an illustrative implementation of a personal thermal control apparatus utilizing two or more heating/cooling modules.

FIG. 5 is an illustrative implementation of a personal thermal control apparatus 400 utilizing two or more heating/cooling modules. A main heating/cooling module 410 in the apparatus may provide a controller board or the like that controls operation of the apparatus. For example, main heating/cooling module 410 may be a heating/cooling module as illustrated in FIG. 2A-2C or 3A-3D. Additional heating/cooling modules 420-1, 420-2, 420-n are simplified modules that do not require a battery, controller board, or user interface, as illustrated in FIGS. 4A-4C. Additional heating/cooling modules 420-1, 420-2, 420-n are each wired to the main heating/cooling module 410, and the additional heating/cooling modules are controlled and powered by the main heating/cooling module. For example, in one embodiment, the apparatus may provide a heating/cooling module on each sleeve of the jacket near the wrist area. The heating/cooling modules may be sewn into the sleeves of the jacket so as to position each heating/cooling module near a wearer's wrist. The main heating/cooling may be provided in the left or right sleeve of the jacket, whereas the other module is a simplified module that is wired through the jacket to the main module.

Figure 6:
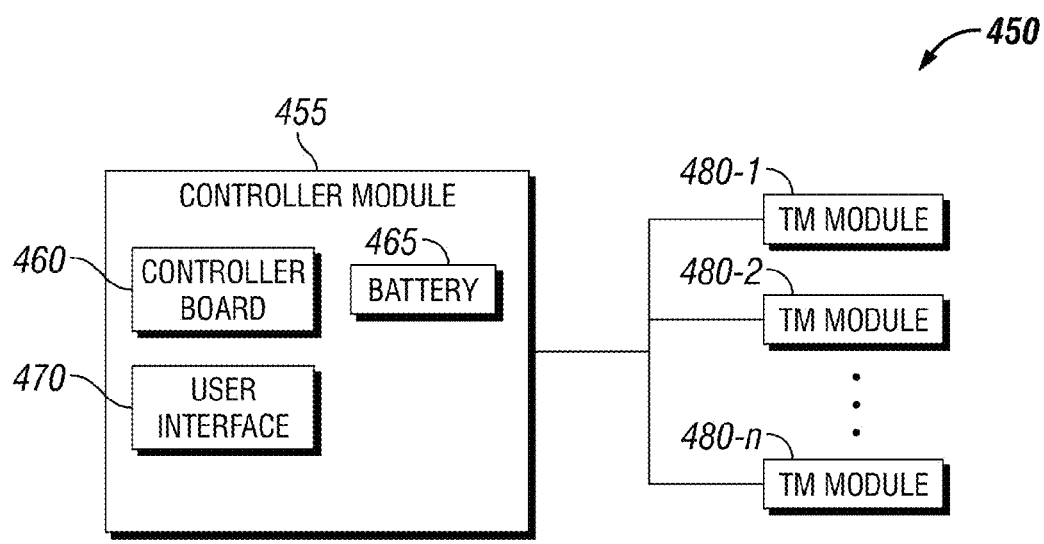
FIG. 6 is an illustrative implementation of another personal thermal control apparatus.

FIG. 6 is an illustrative implementation of another personal thermal control apparatus 450. In other embodiments, a controller module 455 providing a controller board 460, battery 465, and user interface 470 may be provided in a separate controller housing from heating/cooling modules 480-1, 480-2, 480-n. The heating/cooling modules 480-1, 480-2, 480-n are simplified modules that do not require a battery, controller board, or user interface. Each heating/cooling modules 480-

1, 480-2, 480-n is wired to controller module 455, which controls and powers each of the heating/cooling modules.

For example, in one embodiment, two heating/cooling modules may be provided for each sleeve of a jacket, coat, sweater, or the like. The extended even further modules are sewn into the sleeves. The controller module is provided separately in housing that is sewn into another area of the jacket, such as an area near the chest. A wiring harness in the jacket connects each of the heating/cooling modules to the control module.

Figure 7A:
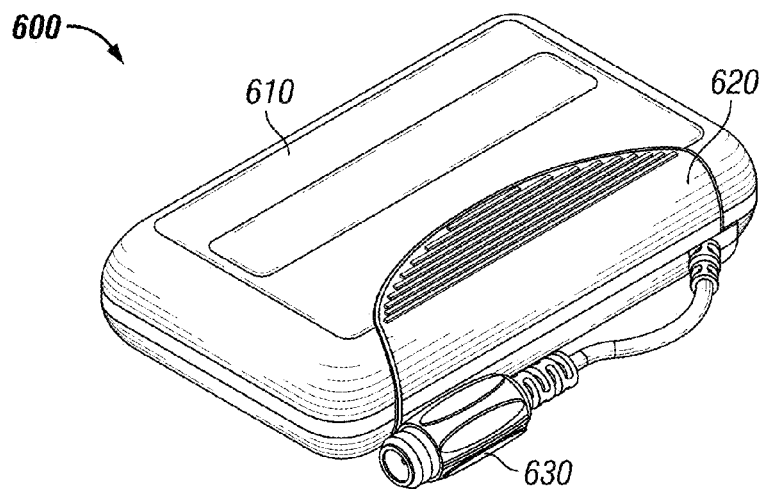
FIGS. 7A-7C are an illustrative implementation of a controller module.
Figure 7B:
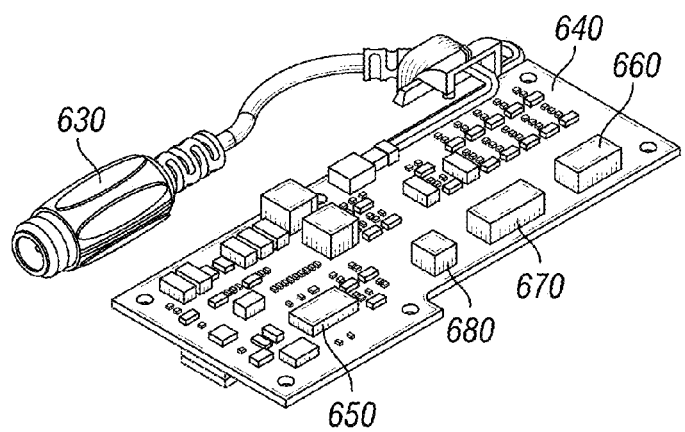
Figure 7C:
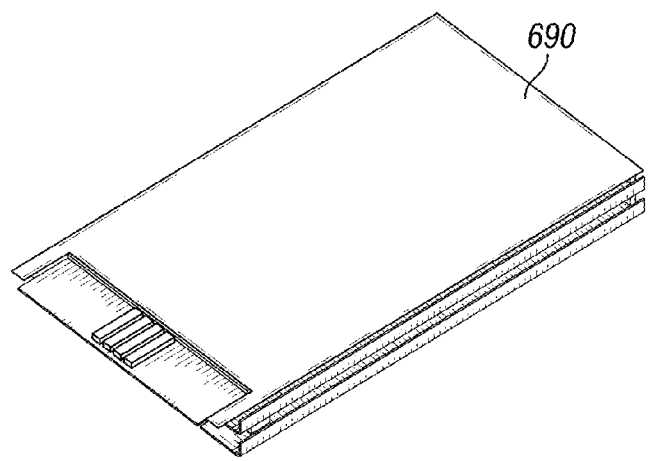

FIGS. 7A-7C is an illustrative implementation of a controller module 600. Controller module may provide a housing 610, pull 620, charge connector 630, controller board 640, microprocessor 650, I/O connector 660, External power connector 670, thermal module connector 680, and battery 690. Housing 610 secures and protects the components of the controller module 600. Pull 620 allows the components of the controller module 600 to be accessed. Charge connector 630 allows the controller module 600 to be connected to an external power source, such as a AC or DC power source.

FIGS. 7B and 7C show components of the controller module 600 without housing 610. Controller board 640 provides the processor 650 for managing and controlling operation of the system. Controller board 640 may also provide I/O connectors 660 that allow buttons or interfaces to be connected. External power connectors 670 allow and external power source to be connected, such as solar cells or an expansion battery pack. TM connector 680 allows the thermal modules to be connected to control board 640. Battery 690 provides power storage for the system.

Figure 8:
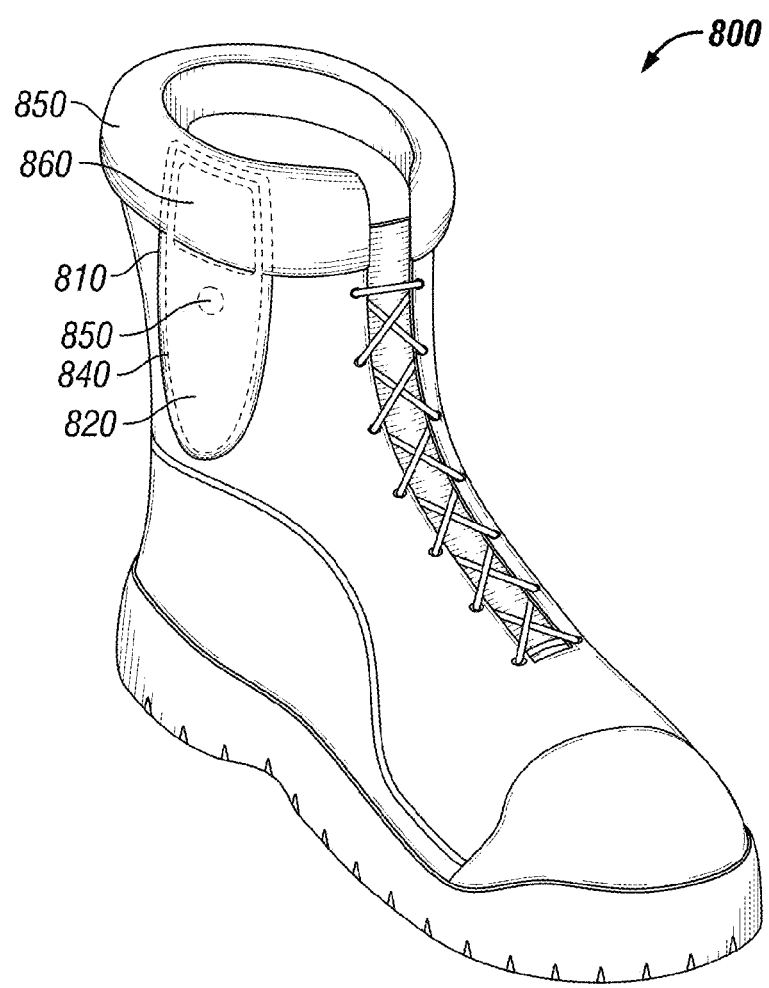
FIG. 8 are an illustrative implementation of a personal thermal control apparatus for footwear.

FIG. 8 is illustrative implementations of a personal thermal control apparatus for footwear. In an embodiment for footwear, each shoe provides a heating/cooling module 800. Heating/cooling module 800 may provide a thermal module 810, controller board 820, plate 840, thermal gel pad 850, and battery 860. As discussed previously, controller board 820 manages operation of various functions of the heating/cooling module 800, such as charging, powering the module, operation modes, and the like. Thermal module 810 heats or cools plate 840 in accordance with the voltage polarity applied to the module. Plate 840 and thermal gel pad 850 provide efficient heat transfer to a user's body. In certain areas of the human body, it may be difficult to manufacture plate 840 in an ergonomic manner that is suitable for efficient heat transfer to the body. Gel pad 850 provides a material that is in a liquid or gel state that displays efficient heat transfer. As the gel pad 850 is liquid or gel, it can easily shape to provide a large area of contact between the region of the human body that the gel pad is positioned near and the gel pad itself. In some embodiments, plate 840 may be omitted, and gel pad 850 serves as the primary means of heat transfer. Heating/cooling module 800 may also optionally provide a photo voltaic patch (not shown) to provide additional power to operate or charge the apparatus.

Figure 9A:
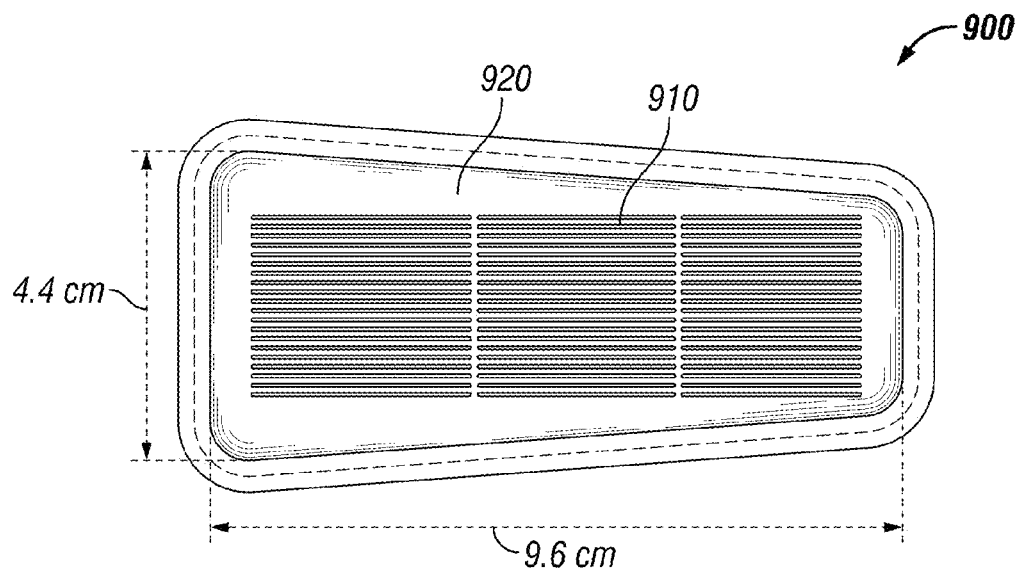
FIGS. 9A-9C are an illustrative implementation of a solar module.
Figure 9B:
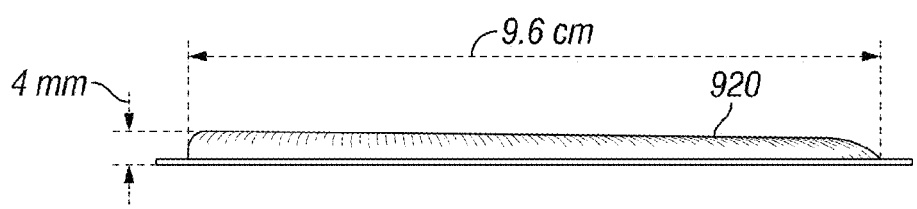
Figure 9C:
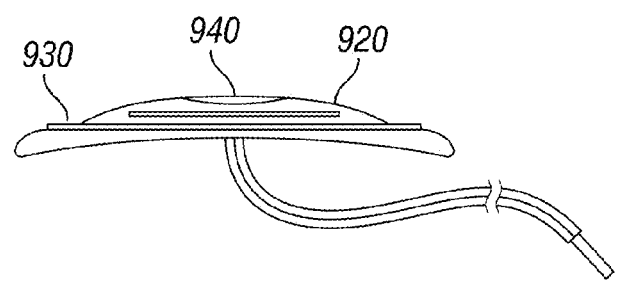

FIGS. 9A-9C is an illustrative implementation of a solar module 900. A photo voltaic panel 910 generating solar energy from exposure to sunlight may be utilized in the personal thermal control apparatus. Photo voltaic panel 910 may provide a holographic background for increased reflectivity to maximize current generation. Housing 920 may be a clear polycarbonate or the like. A lens 940 may be provided by housing 920 to magnify and intensify the light over a small surface area to increase power generation by the photo voltaic cells. For example, lens 940 may be a concave lens. A lip 930 is provided around one or more edges of housing 920. Lip 930 may be utilized for sewing or placing the thermoelectric module 900 into clothing or apparel. Lip 930 may be formed from a suitable material, such as, but not limited to, rubber, sanoprene, TPE or the like. In some embodiments, it may be desirable to combine the solar module with the heating/cooling module or one or more components of the heating/cooling module.

Figure 10A:
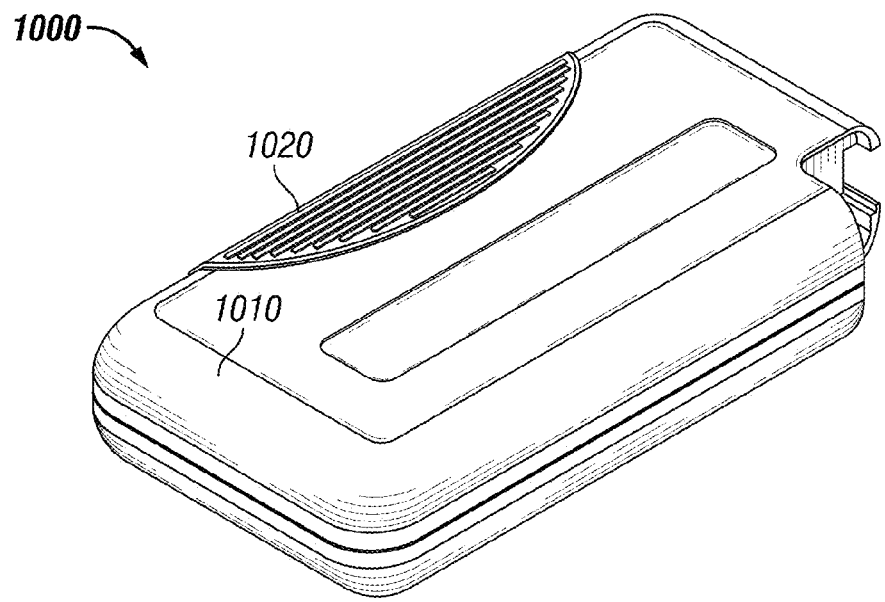
FIGS. 10A-10B are an illustrative implementation of an external battery module.
Figure 10B:
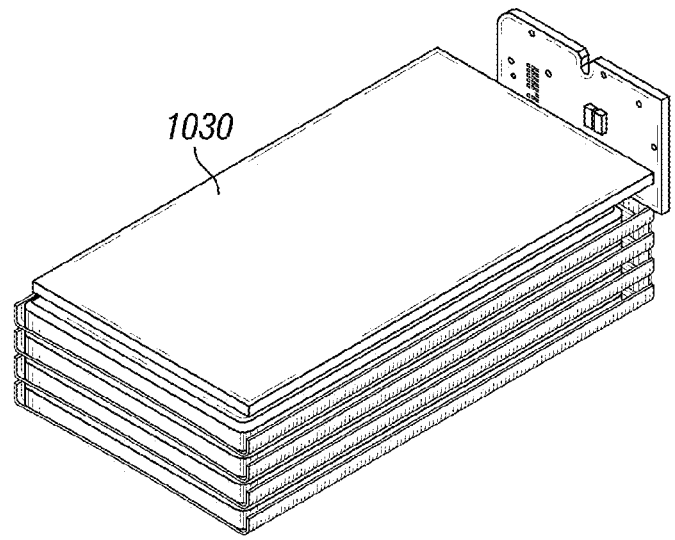

FIGS. 10A and 10B are an illustrative implementation of an external power source 1000. External power source 1000 may provide a housing 1010, pull 1020, and battery 1030. Housing 1010 secures and protects the external power source 1000. Pull 1020 allows the external power source to be accessed. Battery 1030 provides additional power for the system when external power source 1000 is connected to a personal thermal control apparatus.

Figure 11A:
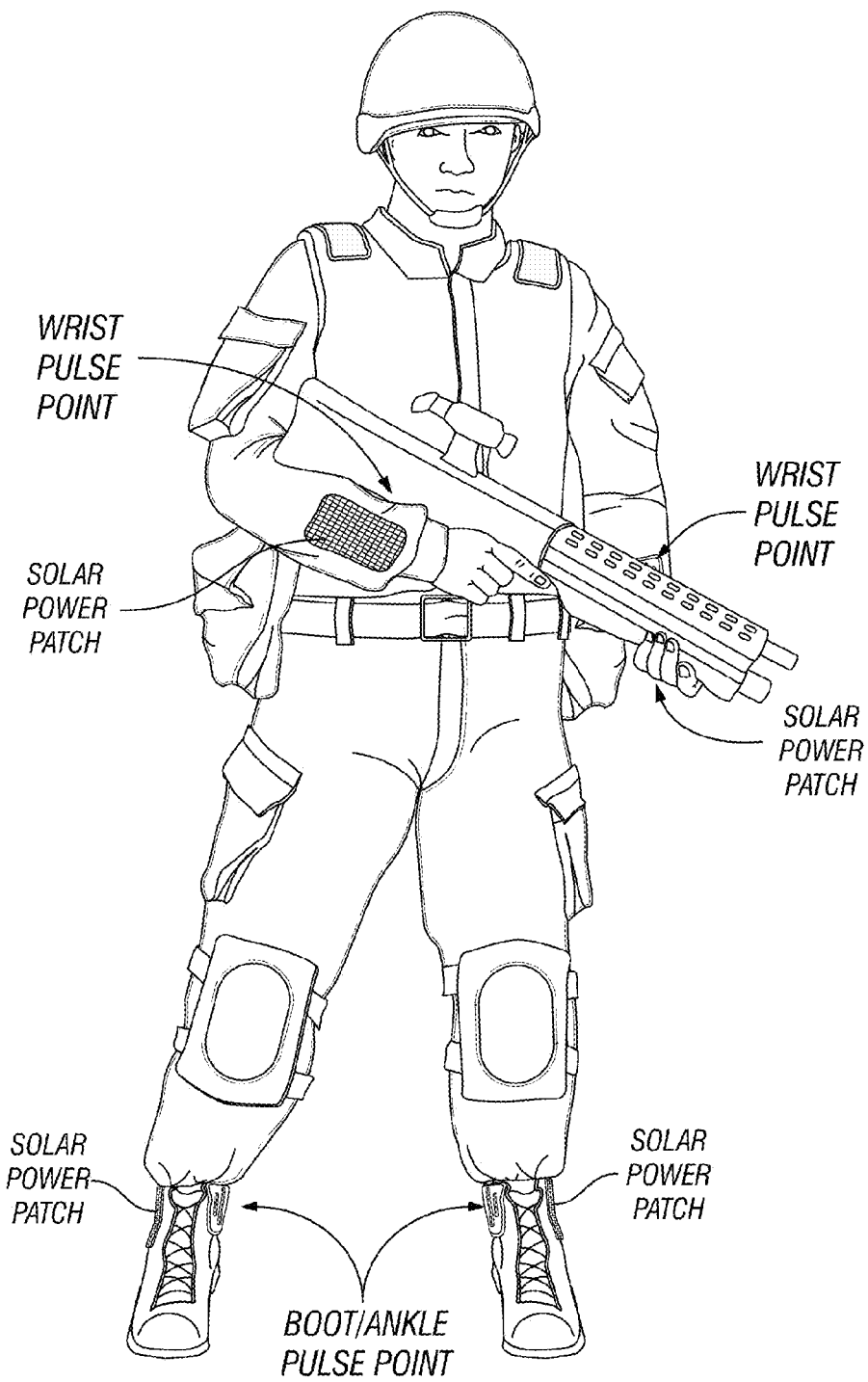
FIGS. 11A and 11B are illustrative implementations of various personal thermal control systems.
Figure 11B:

FIGS. 11A and 11B are illustrative implementations of various personal thermal control systems. The personal thermal control systems discussed herein may be utilized in a variety of application. Nonlimiting examples may include military, athletic, camping, fishing, hiking, outdoor activities, therapeutic medical treatment, or the like. Heating/cooling module(s) may be provided near the wrist, ankles, or any other pulse points on the human body. For example, the heating/cooling module(s) may be provided in apparel, clothing, accessories, jackets, coats, wristbands, footwear, or the like. In some embodiments, an article of clothing may be plugged into another to allow the personal thermal control system to be linked. For example, the personal control system in pants may be plugged into the system provided in a jacket.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure.

What is claimed is:

1. A shoe comprising a personal thermal control apparatus, the personal thermal control apparatus comprising:
 a portable power source;
 a thermal module, wherein the personal thermal control apparatus provides only one thermal module, the thermal module is powered by the power source, a first voltage polarity applied to the thermal module causes a first side of the thermal module to increase in temperature, a second voltage polarity applied to the thermal module causes said first side of the thermal module to decrease in temperature, wherein further the thermal module is positioned in the shoe at a pulse point of an ankle when the shoe is worn to change a core body temperature of a wearer, and the pulse point is an area in close proximity to major vasculature;
 a heat transfer element coupled to said first side of the thermal module; and
 a controller coupled to the power source and the thermal module, wherein the controller manages the voltage applied to the thermal module.

2. The apparatus of claim 1, wherein the power source is a battery, rechargeable battery, or solar cell.

3. The apparatus of claim 1, further comprising:
an on/off button for controlling operation of the apparatus;
a LED indicator displaying information regarding a status of the apparatus; and
a charge port for recharging the power source.

4. The apparatus of claim 1, wherein said heat transfer element is a metal plate or a thermal gel.

5. The apparatus of claim 1, further comprising a compartment containing a thermal gel, wherein said compartment is in contact with said heat transfer element.

6. The apparatus of claim 1, further comprising a heat sink, wherein the heat sink is coupled to a second side of the thermal module opposite said first side.

7. The apparatus of claim 1, further comprising a thermally insulating material positioned adjacent to the thermal module.

8. The apparatus of claim 1, wherein the thermal module is a thermoelectric chip.

9. The apparatus of claim 8, wherein the thermal module further comprises a resistive heating element.

10. The apparatus of claim 1, wherein the portable power source is a 3.7V battery.

11. The apparatus of claim 10, wherein the battery provides sufficient power to operate up to 24 hours.

12. A jacket comprising a personal thermal control apparatus, the personal thermal control apparatus comprising:
a portable rechargeable battery;
a controller coupled to the rechargeable battery and a first thermoelectric chip, wherein the controller manages the voltage applied to a first thermoelectric module;
the first thermoelectric module for heating or cooling is coupled to said controller, the first thermoelectric module comprising
a first housing for securing components of the first thermoelectric module, wherein the first thermoelectric module is positioned in a right sleeve of the jacket at first pulse point of a right wrist when the jacket is worn to change a core body temperature of a wearer;
the first thermoelectric chip positioned in the first housing, wherein the first thermoelectric chip is powered by the rechargeable battery, the first thermoelectric chip is positioned in the jacket at the first pulse point when the jacket is worn to change a core body temperature of a wearer, and the first pulse point is in close proximity to major vasculature; and
a first heat transfer element coupled to a first side of the first thermoelectric chip; and
a second thermoelectric module for heating or cooling coupled to said controller, wherein the second thermoelectric module is positioned in a left sleeve of the jacket at a second pulse point of a left wrist when the jacket is worn to change the core body temperature of the wearer, the second thermoelectric module comprising
a second housing separate from said first housing, wherein the second housing secures components of the second thermoelectric module;
a second thermoelectric chip positioned in the second housing, wherein the second thermoelectric chip is powered by the rechargeable battery, the second thermoelectric chip is positioned in the jacket at the second pulse point when the jacket is worn to change the core body temperature of the wearer, and the second pulse point is in close proximity to major vasculature; and
a second heat transfer element coupled to a first side of the second thermoelectric chip.

13. The apparatus of claim 12, further comprising at least one solar cell coupled to the controller, wherein the solar cell generates energy that is stored by the rechargeable batteries.

14. The apparatus of claim 12, wherein said first heat transfer element is a metal plate or a thermal gel or both.

15. The apparatus of claim 12, further comprising a heat sink, wherein the heat sink is coupled to a second side of the first thermoelectric chip opposite said first side.

16. The apparatus of claim 12, further comprising a thermally insulating material positioned adjacent to the first thermoelectric chip.

17. The apparatus of claim 12, wherein the portable rechargeable battery is a 3.7V battery.

18. The apparatus of claim 17, wherein the battery provides sufficient power to operate up to 24 hours.

19. The apparatus of claim 12, wherein the first thermoelectric module further comprises a resistive heating element.

20. The apparatus of claim 12, wherein the first thermoelectric module further comprises a connector coupling the first thermoelectric module to the controller.

\* \* \* \* \*